(12) United States Patent
Darr et al.

(10) Patent No.: US 6,995,377 B2
(45) Date of Patent: Feb. 7, 2006

(54) PROCESS AND APPARATUS FOR TESTING BOTTLES

(75) Inventors: Richard C. Darr, Medina, OH (US); Joy Lynn Hubbard, Hinckley, OH (US); Thomas Jackson Simpson, Marshallville, OH (US)

(73) Assignee: Plastipak Packaging, Inc., Plymouth, MI (US)

( * ) Notice: Subject to any disclaimer, the term of this patent is extended or adjusted under 35 U.S.C. 154(b) by 282 days.

(21) Appl. No.: 10/619,132

(22) Filed: Jul. 14, 2003

(65) Prior Publication Data

US 2004/0065841 A1    Apr. 8, 2004

Related U.S. Application Data

(60) Provisional application No. 60/401,079, filed on Aug. 2, 2002.

(51) Int. Cl.
    *G01J 21/59*    (2006.01)

(52) U.S. Cl. .................................................. 250/372
(58) Field of Classification Search .................. None
    See application file for complete search history.

(56) References Cited

U.S. PATENT DOCUMENTS 5,331,167 A * 7/1994 Hoshino et al. ............ 250/372
5,991,018 A * 11/1999 Imaizumi et al. ........ 356/239.1

FOREIGN PATENT DOCUMENTS

JP          10024092 A  *  1/1998

* cited by examiner

*Primary Examiner*—Constantine Hannaher
(74) *Attorney, Agent, or Firm*—Robert H. Bachman

(57)    ABSTRACT

Process and apparatus for testing the coating thickness on a container by shining ultraviolet light through the container to at least one sensor.

20 Claims, 2 Drawing Sheets

PROCESS AND APPARATUS FOR TESTING BOTTLES

CROSS REFERENCE TO RELATED APPLICATIONS

This application is based on provisional application Ser. No. 60/401,079, filed Aug. 2, 2002.

BACKGROUND OF THE INVENTION

The present invention relates to plastic containers, preferably for non-carbonated food products. More particularly, the present invention relates to molded plastic containers, such as injection molded and/or blow molded plastic containers, having a layered or coated structure, especially having a coating on the internal surface thereof, as a carbon coating.

It is highly desirable to provide an effective and low cost way of overcoming the porosity of plastic containers and the problems attendant thereon.

Plastic containers and multi-layered plastic containers are commonly used for packaging items in a wide range of fields, including food and beverage, medicine, health and beauty, and home products. Plastic containers are known for being easily molded, cost competitive, lightweight, and are generally suitable for many applications. Multi-layered plastic containers provide the benefit of being able to use different materials in each of the layers, wherein each material has a specific property adapted to perform a desired function.

Because plastic containers may permit low molecular gases, such as oxygen and carbon dioxide, to slowly permeate through their physical configurations, the use of plastic containers sometimes proves to be less desirable when compared to containers formed from other less permeable materials, such as metal or glass. In most applications, the shelf life of the product contents is directly related to the package's ability to effectively address such molecular permeation. In the case of non-carbonated beverages, such as juices, oxygen in the atmosphere surrounding the container can gradually permeate inwardly through the plastic walls of the container to reach the inside of the container and deteriorate the contents. A highly porous container can permit rapid deterioration of the flavor of the container contents.

To address some to the foregoing concerns, plastic container manufacturers have utilized various techniques to reduce or eliminate the absorption and/or permeability of gases in plastic containers. Some of the more common techniques include: increasing the thickness of all or portions of the walls of the container; incorporating one or more barrier layers into the wall structure; including oxygen-scavenging or reacting materials within the walls of the container; and applying various coatings to the internal and/or external surface of the container. However, a number of conventional barrier and/or scavenger materials will not effectively curtail permeation through a highly porous container wall, especially over extended periods of time. Moreover, there are usually other practical concerns associated with most conventional techniques, most commonly, increased material costs and/or production inefficiencies.

In recent times, the use of plastics has become a significant social issue. Recycling has become an increasingly important environmental concern and a number of governments and regulatory authorities continue to address the matter. In a number of jurisdictions, legislation pertaining to the collection, return, and reuse of plastic containers has either been considered or has already been enacted. However, recycled material generally cannot be used in contact with the contents of most containers.

It is highly desirable to provide an effective, efficient and low cost process for coating the internal surface of a plastic container to address the foregoing problems and if desired permit the use of recycled content in the outer layer or layers of the container.

Processes have been developed for coating the internal surface of a container, as with a thin carbon coating, in order to address these problems. However, it is desirable to carefully control the thickness parameters of the coating.

Therefore, a need exists in the industry and it is an object of the present invention to provide a process and apparatus for use in the coating process of a plastic container in the testing of the coating parameters, especially the internal surface thereof, as for example, with a carbon coating.

It is a further object of the present invention to provide a process and apparatus as aforesaid which is effective, efficient and low cost.

Further objects and advantages of the present invention will appear hereinbelow.

SUMMARY OF THE INVENTION

It has been found that the foregoing objects and advantages are readily obtained in accordance with the present invention.

The present invention recognizes the problems and concerns associated with conventional multi-layered or coated plastic containers, especially those used to hold carbonated or non-carbonated food products, such as beverages, and advantageously provides an improved process and apparatus for providing an effective coated container with coating parameters carefully controlled. A container constructed in accordance with the principles of the present invention provides several advantages over those previously available. Such advantages are generally realized through the use of a coating procedure and the testing thereof in accordance with the present invention, especially a carbon coating, on the internal surface of the container. It is a significant advantage of the present invention that one may desirably also include oxygen scavengers and may have a multilayered configuration and also may provide different coatings and effectively test the coating parameters in accordance with the present invention. Furthermore, the present process and apparatus may use conventional processing techniques and manufacturing equipment.

An important aspect of the present invention is that one may obtain effective barrier properties in the present container prepared in accordance with the present invention. Further, the ease in subsequently recycling a container produced in accordance with the principles of the present invention make the practice of the invention extremely advantageous. Moreover, the present invention provides the additional advantage of permitting the manufacturer to controllably vary the material positioning and wall thickness at any given location along the vertical length of the inner and/or outer layers of the container and obtain desirably controlled properties.

In accordance with the principles of the present invention, a container is provided which is particularly suitable for non-carbonated food products, as beverages, which may for example be blow molded or extrusion molded. The container generally has an open mouth, upper wall portion, an intermediate sidewall portion positioned beneath the upper wall portion, and a base portion positioned beneath the intermediate sidewall portion, the base portion being adapted to dependently or independently support the container. The container preferably includes a molded first layer having an inner surface and an outer surface formed from any desired plastic and which may include recycled content, and a coating formed adjacent and desirably on the inner surface of the first layer and adhered thereto and substantially coextensive with the first layer, desirably a carbon coating. In a preferred embodiment, the thickness of the first layer is controllably adjusted along its vertical length. If desirable, the first layer may also include additional barrier materials and/or oxygen scavenging/reacting materials incorporated therein.

In accordance with the principles of the present invention, the container may include a second layer adjacent the first layer, wherein the second layer is adjacent at least one of the inner surface of the first layer and the outer surface of the first layer, to provide a highly desirable, multi-layered container.

The container of the present invention is particularly suitable for use with carbonated or non-carbonated products as food products, but may also be used for other products, as for example products which advantageously include the injection of gases therein, as CO2 or nitrogen.

In accordance with the present invention, the container is initially coated as desired in a first stage, preferably an internal carbon coating. The first stage coats the container, preferably the internal surface thereof, with the desired thickness of the coating. If a carbon coating is used, the carbon coating preferably has a thickness of from 0.01 to 20 microns and desirably from 0.05 to 10 microns, and the coating may if desired be of uniform thickness or of variable thickness.

The second stage of the present invention is to determine effectively and efficiently the accuracy of the coating thickness in the first stage. It is clearly highly desirable that this be done since the coating thickness should generally be accurate within a desired range. This is determined in accordance with the present invention by shining ultraviolet (UV) light through the container and determining by one or more sensors how much light passes through the coating. For example, a rod maybe inserted inside the coated container which shines ultraviolet light through the coating to one or more sensors located outside the container. A plurality of these sensors may be used in order to determine the thickness of the coating at various points along the container, or a simple sensor which may be movable along the vertical length of the container. The container is desirably rotated so that all portions of the container are directly adjacent the sensor or sensors.

Thus, the present invention can accurately and quickly and in line with the coating procedure determine whether or not the containers have a suitable thickness coating along the length thereof.

Other and further advantages and novel features of the present invention are readily apparent from the following detailed description of the best mode for carrying out the invention when taken in connection with the accompanying drawings, wherein, by way of illustration and example, representative embodiments of the present invention are disclosed.

BRIEF DESCRIPTION OF THE DRAWINGS

The present invention will be more readily understandable from a consideration of the accompanying drawings, wherein.

DETAILED DESCRIPTION OF PREFERRED EMBODIMENTS

Figure 1:
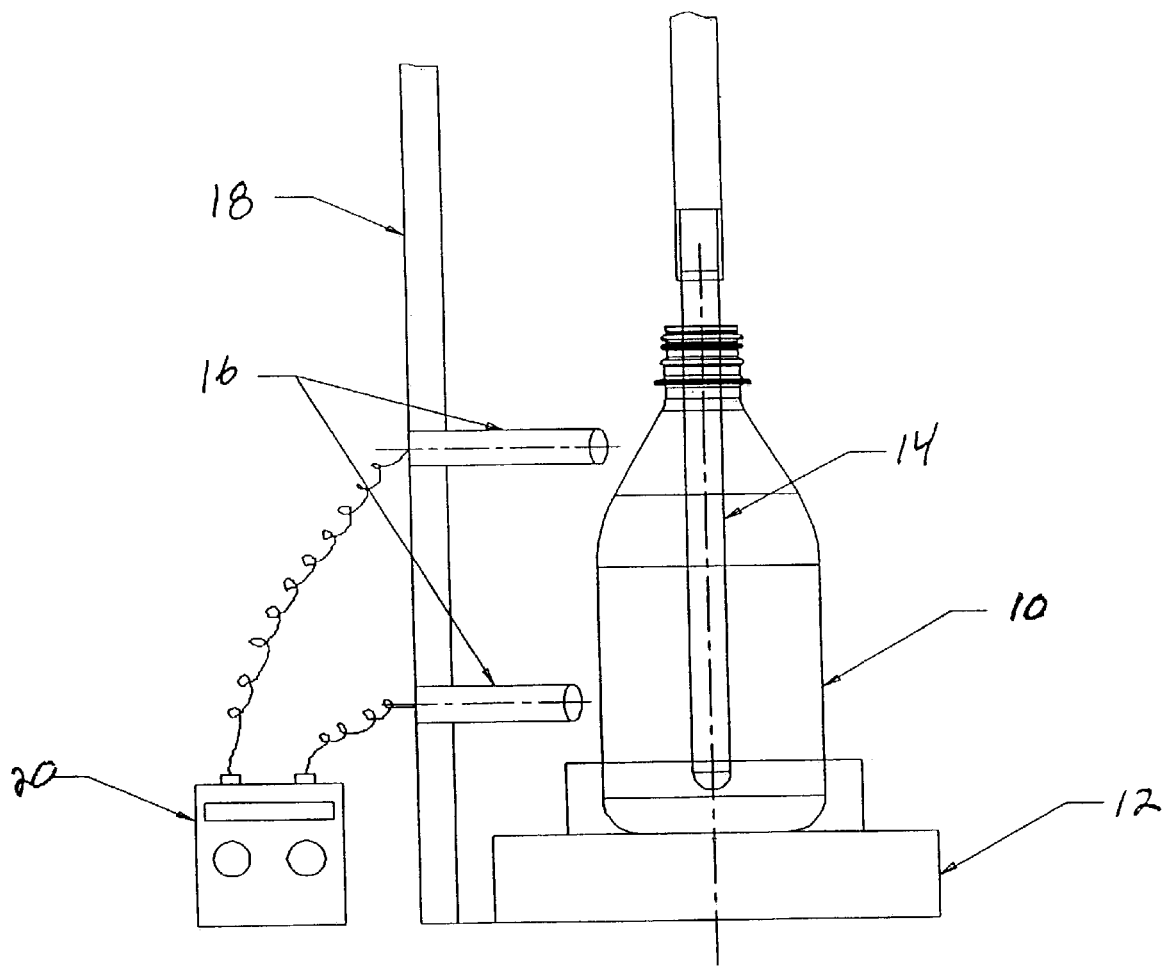
FIG. 1 is an illustrative view illustrating one embodiment of the process and apparatus of the present invention.

Referring now to the drawings in detail, FIG. 1 shows a representative embodiment of the present invention. A bottle 10 is provided with a coating or layer on the internal surface thereof. For example, the bottle may have been previously coated with a carbon coating in a first stage, as for example by the use of acetylene gas on the internal surface thereof. Representative procedures for carbon coating are shown in U.S. Pat. Nos. 6,475,579, 6,495,226 and 6,461,699.

Naturally, other materials may be used for coating the container, and the coating may be provided on the external surface if desired. For example, a desired UV inhibitor may be effectively spray coated on the internal surface of the container.

The coated container 10 is transferred desirably from the coating step to a rotary table 12. Rod 14 is inserted in the container and shines ultraviolet light through the coated internal surface of the container to one or more ultraviolet sensors 16 located outside the container and supported by framework or linear rail 18. Sensors 16 are connected to meter 20 which accurately measures the amount of light shining through the coated surface at one or more locations along the internal surface of the container. For example, dual meter 20 can read both sensors. This effectively determines the thickness of the coating at one or more locations of the container where desired and effectively determines whether or not the coating process complies with desired standards. The rotation of the container 10 on rotary table 12 effectively determines the coating thickness along the entire circumferential surface of the container. If desired, the container can be held by the neck and rotated by the neck. The sensors can if desired be moved up and/or down, as on a linear rail, for further readings along the vertical length of the container.

If desired, the ultraviolet sensors can be connected to a computer which is operatively connected to the coating process and which can immediately vary the coating procedure in order to overcome any excess or insufficient coating thickness as determined by the ultraviolet sensors 16.

The process and apparatus of the present invention is desirably selective so that not all bottles are tested, although of course this can be done if necessary or desired.

Alternatively, if the testing procedure determines an unacceptable variation in coating thickness, one can simply stop the coating line and vary the coating procedure as desired and then restart the line followed by further testing to determine coating accuracy.

Thus, the present invention shines UV light through a coated container to one or more ultraviolet sensors, and thereby obtains a reading as to the thickness of the coating to readily determine accuracy of coating thickness. The process and apparatus described hereinabove is reliable and accurate and can readily determine unacceptable coating levels.

Moreover, the process and apparatus of the present invention enables one to readily increase or decrease the coating time or temperature or any variable that effectively impacts coating thickness, and this can be done quickly, conveniently and expeditiously on a commercial scale to obtain the desired commercial product. Moreover, the present invention is readily usable with virtually any plastic container in a commercial operation, such as a coated monolayer or coated multilayer container.

In a preferred operation, the containers are removed from a high speed rotary molding machine and subsequently transferred directly or indirectly to an apparatus for applying the coating to the containers, as a carbon coating. In high speed production applications, a coating procedure, as a carbon coating apparatus, will typically also be on the rotary type. One or more coated containers is then transferred from the coating line to the testing apparatus of the present invention in order to determine whether or not the coating in the coated container meets coating thickness parameters.

A representative method for carbon-coating multi-layer containers 10 is next described in further detail. In accordance with a preferred method for carbon coating the inner surface of the container, a conventional carbon-coating or carbon-treating apparatus having rotary kinematics and a central vertical axis is provided. The carbon-coating apparatus generally rotates about its central vertical axis in a first rotational direction, e.g., counterclockwise, at a fairly high rotational speed. A blow-molding machine, or other rotary container transfer mechanism, located generally in close proximity to the carbon-coating apparatus functions as the source of containers for subsequent carbon-coating treatment. To facilitate the transfer, the rotary container transfer mechanism rotates in a direction opposed to the rotational direction of the carbon-coating apparatus, e.g., clockwise, and the multi-layer containers are mechanically shifted from the container transfer mechanism to the carbon-coating apparatus. Although not required for the practice of the present invention, the container preferably includes a neck flange or other physical means for at least partially supporting the container during the mechanical transfer process.

As the containers are transferred from the transfer mechanism to the carbon-coating apparatus, the containers are preferably held by the upper portion in an upright orientation with the opening generally facing upwardly. If desired, a vacuum can also be generated and used to support or partially support the container. During the transfer process, the individual containers are received by a receiving mechanism which is part of the carbon-coating apparatus. The receiving mechanism revolves around the central axis of the carbon-coating apparatus, grasps or secures the container, and seals the opening of the upper portion of the container, much like a lid. When properly positioned over and abutting the opening, the receiving mechanism produces a tight to "airtight" seal over the container.

The receiving mechanism includes at least two apertures positioned above the opening of the container that are used for the introduction and removal of gases from the inside of the container. A first aperture in the receiving mechanism is in communication with a vacuum source, such as a vacuum pump. After the receiving mechanism has securely sealed the opening, the air within the container is discharged through the first aperture by means of a vacuum. It is desirable that degree of vacuum falls within a range of about $10^{-2}$ to $10^{-5}$ torr, so as to shorten the discharge time for a vacuum and saves necessary energy therefor. With a lower degree of vacuum of over $10^{-2}$ torr, impurities in the container are much increased, on the other hand, with a higher degree of vacuum under $10^{-5}$ torr, increased time and a large energy are needed to discharge the air in the container.

Once the air inside the container has been evacuated, the container is subsequently filled or "charged" with a raw gas that will be used in the formation of the carbon coating. The flow rate of the raw gas is preferably within a range from about 1 to 100 ml/min. Preferably, the diffusion of the raw gas within the container is enhanced by providing an extension, such as a tube having a plurality of blow openings. In accordance with one embodiment, an extension enters inside of the container through the second aperture some time after the opening is sealed and the extension extends to within about 25.4 mm to 50.8 mm (1.0 in.–2.0 in.) of the lowermost portion of the container.

The raw gas may be comprised of aliphatic hydrocarbons, aromatic hydrocarbons, oxygen containing hydrocarbons, nitrogen containing hydrocarbons, etc., in gaseous or liquid state at a room temperature. Benzene, toluene, o-xylene, m-xylene, p-xylene and cyclohexane each having six or more than six carbons may desirably be used. The raw gases may be used singularly, but a mixture of two or more than two kinds of raw gases can also be used. Moreover, the raw gases may be used in the state of dilution with inert gas such as argon and helium.

At some point after the container has been received by the receiving mechanism of the carbon-coating apparatus, the container is inserted into a cylinder or other hollow space provided to accommodate the container. In the preferred embodiment, the carbon-coating apparatus includes a plurality of hollow cylinders that rotate in the same direction as, and in synchronization with, the receiving mechanism. It is further preferred that the receiving mechanism that retains and seals the opening of the container also functions to cover the cylinder.

After the supply of the raw gas into the container, energy is impressed upon the container from a high frequency electric energy source, such as a microwave-producing device. The impression of the electric power generates plasma, and causes extreme molecular excitation ionization and a carbon coating to be formed on the inner surface of the container in a desired coating thickness.

While the foregoing method illustrates one process for forming a carbon coating on the inner surface of a container, other conventional methods can also be used successfully and other materials can be used to coat the container. For instance, the plastic container could instead be inserted and accommodated within an external electrode and have an internal electrode positioned within the container. After the container is evacuated and is charged with raw gas supplied through the internal electrode, electric power is supplied from the high frequency electric source to the external electrode. The supply of electric power generates plasma between the external electrode and the internal electrode. Because the internal electrode is earthed, and the external electrode is insulated by the insulating member, a negative self-bias is generated on the external electrode, so that carbon film is formed uniformly on the inner surface of the container along the external electrode.

When the plasma is generated between the external electrode and the internal electrode, electrons are accumulated on the inner surface of the insulated external electrode to electrify negatively the external electrode, to generate negative self-bias on the external electrode. At the external electrode, a voltage drop occurs because of the accumulated electrons. At this time, carbon dioxide as the carbon resource exists in the plasma, and positively ionized carbon resource gas is selectively collided with the inner surface of the container which is disposed along the external electrode, and, then, carbons close to each other are bonded together thereby to form a hard carbon film comprising a remarkably dense coating on the inner surface of the container.

The thickness and uniformity of the carbon coating can be readily varied, as for example by adjusting the output of high frequency; the pressure of the raw gas in the container; the flow rate for charging the container with gas; the period of time during which plasma is generated; the self-bias and kind of raw materials used; adjusting treatment wattage; adjusting treatment time; and other like variables. Atmospheric conditions may have an effect on the coating process, including but not limited to air temperature, humidity, and barometric pressure. Therefore, the atmospheric conditions may be controlled to vary the coating process. However, the thickness of the carbon coating is preferably within a range from 0.01 to 20 microns and desirably from 0.05 to 10 microns to obtain the effective suppression of the permeation and/or absorption of the low molecular organic compound and the improved gas barrier property, in addition to an excellent adhesion to plastic, a good durability and a good transparency. The present invention simply and expeditiously tests the accuracy of the coating parameters, and this can be done in-line with the coating procedure.

As indicated hereinabove, the present invention is readily useable with other materials coated on the container, such as other UV inhibitors.

After the coating procedure, one or more of the coated containers is then transferred to the testing stage as indicated hereinabove.

Moreover, as indicated hereinabove, the container prepared in accordance with the present invention can readily include recycled content since the outer layer does not come in contact with the contents of the container. Any desired amount of recycled plastic can readily be blended into the outer layer.

Moreover, a variety of colors may readily be used for the outer layer or layers. Naturally, one must adjust UV light transmission parameters in the testing procedure to accommodate color changes in the outer layer.

Figure 2:
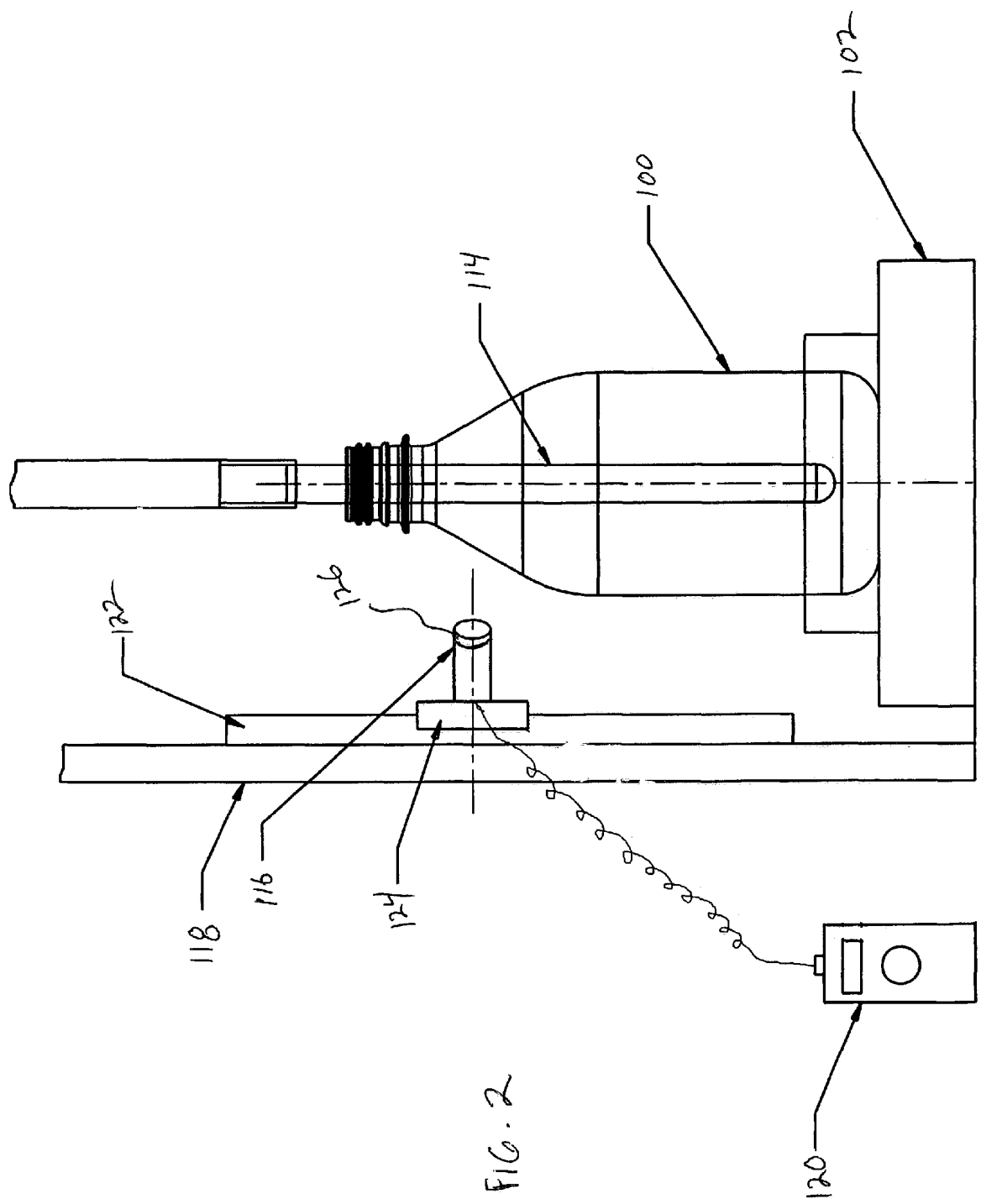
FIG. 2 is an illustrative view illustrating a further embodiment of the present invention.

FIG. 2 shows an advantageous alternate embodiment of the present invention. FIG. 2 shows a bottle 100 provided with a coating on the internal surface thereof, as a carbon coating. As with FIG. 1, the coated container 100 is desirably transferred from the coating step to rotary table 102. Rod 114 is inserted in the container and shines UV light through the coated internal surface of the container to a single UV sensor 116 supported on framework 118. The sensor 116 is connected to meter 120 which accurately measures the amount of light shining through the coated surface and thereby effectively determines the thickness of the coating. Sensor 116 is mounted on a linear rail 122 via linear bearing 124. The linear rail is mounted on framework 118. The sensor may be manually or automatically moved along linear rail 122 to determine coating thickness at various locations. One could provide adjustable stops on the linear rail to obtain readings at pre-set locations. A single sensor removes the possibility of sensor variability with two or more sensors; however, a single sensor would take slightly more time to obtain readings. For example, a single sensor may take 1.5–3 minutes, while two or more sensors may take 45 seconds to 1.5 minutes.

The UV light can be provided by a bulb, light emitting diode (LED), or any desired source. Also, for example, the UV light source can be outside the container, exposed to a liquid receptor and transmitted to a tube like member which is inserted in the container. This avoids inserting an LED into the container.

The UV wave length can be varied depending on the coating to be measured, with the wave length appropriate to the particular coating or layer to be measured. For example, for a carbon coating on polyethylene terephthalate (PET), the UV wave length should range from 350 to 380 nanometers, and is preferably about 365 nanometers.

The bottle color is not especially germane; however, the present invention would be most effective for a coating or layer on a relatively clear or colorless container.

It may be advantageous to include a lens or magnifier over the sensor, as lens 126 over sensor 116, to focus the light passing through the container on the sensor.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope.

What is claimed is:

1. Process for testing the thickness of a coating on a container, which comprises: providing a container having a carbon coating on the internal surface of the container; positioning means inside the container which shines ultraviolet light through the container; positioning at least one ultraviolet light sensor outside of the container and passing the ultraviolet light from the inside of the container through the container to the sensor; and determining the thickness of the coating by said at least one sensor which determines how much light passes through the container.

2. The process of claim 1, wherein the container is a plastic container having an open mouth, an intermediate sidewall and a base adapted to support the container.

3. The process of claim 2, wherein a rod is inserted inside the container which shines ultraviolet light through the container to said at least one sensor.

4. The process of claim 2, including positioning at least two of said sensors outside of the container along the vertical length of the container.

5. The process of claim 2, wherein said at least one sensor is movable along the vertical length of the container.

6. The process of claim 2, wherein the container is rotated so that said at least one sensor is exposed to the entire circumference of the container.

7. The process of claim 2, wherein said at least one sensor is connected to a meter which measures the amount of light passing through the coating.

8. The process of claim 2, wherein the thickness of the carbon coating is from 0.01 to 20 microns, and the UV wave length is from 350 to 380 nanometers.

9. The process of claim 2, including a lens over the sensor to focus the light passing through the container on the sensor.

10. The process of claim 2, wherein the testing is associated with a carbon coating apparatus so that coating defects can be readily corrected.

11. Apparatus for testing the thickness of a coating on a container, which comprises: a container having a carbon coating on the internal surface of the container; means inside the container which shines ultraviolet light through the container; at least one ultraviolet light sensor outside of the container, wherein said ultraviolet light passes from the inside of the container through the container to the sensor; wherein said sensor is operative to determine how much light passes through the container, thereby determining the thickness of the coating.

12. Apparatus according to claim 11, wherein the container is a plastic container having an open mouth, an intermediate sidewall and a base adapted to support the container.

13. Apparatus according to claim 12, including a rod inside the container which shines ultraviolet light through the container to said at least one sensor.

14. Apparatus according to claim 12, including at least two of said sensors outside of the container along the vertical length of the container.

15. Apparatus according to claim 12, wherein said at least one sensor is movable along the vertical length of the container.

16. Apparatus according to claim 12, including means to rotate the container so that said at least one sensor is exposed to the entire circumference of the container.

17. Apparatus according to claim 12, including a meter connected to said at least one sensor which measures the amount of light passing through the container.

18. Apparatus according to claim 12, wherein the thickness of the carbon coating is from 0.01 to 20 microns and the UV wave length is from 350 to 380 nanometers.

19. Apparatus according to claim 12, including a lens over the sensor to focus the light passing through the container on the sensor.

20. Apparatus according to claim 12, including an associated carbon coating apparatus so that coating defects can be readily corrected.

* * * * *